(12) United States Patent
Tearney et al.

(10) Patent No.: US 11,519,712 B2
(45) Date of Patent: Dec. 6, 2022

(54) SYSTEMS AND METHODS FOR AN ACTIVELY CONTROLLED OPTICAL IMAGING DEVICE

(71) Applicant: The General Hospital Corporation, Boston, MA (US)

(72) Inventors: Guillermo J. Tearney, Cambridge, MA (US); Kanwarpal Singh, Weymouth, MA (US)

(73) Assignee: The General Hospital Corporation, Boston, MA (US)

( * ) Notice: Subject to any disclaimer, the term of this patent is extended or adjusted under 35 U.S.C. 154(b) by 586 days.

(21) Appl. No.: 16/314,044

(22) PCT Filed: Jul. 5, 2017

(86) PCT No.: PCT/US2017/040701
§ 371 (c)(1),
(2) Date: Dec. 28, 2018

(87) PCT Pub. No.: WO2018/009529
PCT Pub. Date: Jan. 11, 2018

(65) Prior Publication Data
US 2021/0223026 A1    Jul. 22, 2021

Related U.S. Application Data

(60) Provisional application No. 62/516,853, filed on Jun. 8, 2017, provisional application No. 62/358,525, filed on Jul. 5, 2016.

(51) Int. Cl.
*G01B 9/02091* (2022.01)
*A61B 1/00* (2006.01)
(Continued)

(52) U.S. Cl.
CPC ...... *G01B 9/02091* (2013.01); *A61B 1/00117* (2013.01); *A61B 1/00165* (2013.01);
(Continued)

(58) Field of Classification Search
CPC .............. G01B 9/0205; G01B 9/02057; G01B 9/02091
See application file for complete search history.

(56) References Cited

U.S. PATENT DOCUMENTS

| 5,237,630 A | 8/1993 | Hogg et al. |
| 6,839,483 B2 | 1/2005 | Reed et al. |

(Continued)

FOREIGN PATENT DOCUMENTS

| JP | 2015062639 A | 4/2015 |
| WO | 2005047813 A1 | 5/2005 |
| WO | 2009019847 A1 | 2/2009 |

OTHER PUBLICATIONS

Armstrong et al., Quantitative Upper Airway Imaging with Anatomic Optical Coherence Tomography, American Journal of Respiratory and Critical Care Medicine, 2006, 173(2):226-233.
(Continued)

*Primary Examiner* — Michael A Lyons
(74) *Attorney, Agent, or Firm* — Quarles & Brady LLP

(57) ABSTRACT

The present disclosure provides a common-path optical waveguide probe. The common-path optical waveguide probe includes an optical waveguide, a lens, and a reference reflector. The optical waveguide includes a proximal end and a distal end. The lens is coupled to the distal end. The reference reflector is positioned between the optical waveguide and the lens. The disclosure also provides a catheter and an optical coherence tomography system utilizing the
(Continued)

common-path optical waveguide probe. The disclosure also provides methods of making and using the common-path optical waveguide probe.

24 Claims, 16 Drawing Sheets

(51) Int. Cl.
　　　*A61B 5/00*　　　(2006.01)
　　　*G01B 9/02*　　　(2022.01)
(52) U.S. Cl.
　　　CPC .......... *A61B 5/0066* (2013.01); *G01B 9/0205* (2013.01); *A61B 2562/0233* (2013.01)

(56) References Cited

U.S. PATENT DOCUMENTS

| | | | |
|---|---|---|---|
| 7,608,463 | B2 | 10/2009 | Saaski |
| 7,706,646 | B2 | 4/2010 | Wang et al. |
| 7,952,719 | B2 | 5/2011 | Brennan, III |
| 9,087,368 | B2 | 7/2015 | Tearney et al. |
| 2002/0122246 | A1 | 9/2002 | Tearney et al. |
| 2005/0018201 | A1 | 1/2005 | de Boer et al. |
| 2006/0044566 | A1 | 3/2006 | Li |
| 2006/0093276 | A1 | 5/2006 | Bouma et al. |
| 2006/0274323 | A1 | 12/2006 | Gibler et al. |
| 2007/0147738 | A1 | 6/2007 | Wang et al. |
| 2008/0144040 | A1 | 6/2008 | Drabarek et al. |
| 2010/0134802 | A1 | 6/2010 | Chan et al. |
| 2011/0112591 | A1 | 5/2011 | Seymour et al. |
| 2012/0101374 | A1* | 4/2012 | Tearney .............. G01N 21/6456 600/427 |
| 2012/0243251 | A1* | 9/2012 | Suzuki ................... A61B 1/055 362/551 |
| 2013/0023760 | A1 | 1/2013 | Liu et al. |
| 2013/0190565 | A1 | 7/2013 | Gora et al. |
| 2013/0310643 | A1 | 11/2013 | Gora et al. |
| 2013/0331709 | A1 | 12/2013 | Le et al. |
| 2014/0153864 | A1* | 6/2014 | Sinclair ................... G02B 23/26 385/12 |
| 2014/0160482 | A1* | 6/2014 | Tearney ................ A61B 5/0066 356/451 |
| 2014/0160486 | A1 | 6/2014 | Kang et al. |
| 2014/0185042 | A1 | 7/2014 | Baets et al. |
| 2017/0068057 | A1* | 3/2017 | Fiebig ................... G02B 6/4214 |
| 2018/0192880 | A1* | 7/2018 | Patel ..................... A61B 5/0084 |

OTHER PUBLICATIONS

Boppart et al., Optical Coherence Tomography: Feasibility for Basic Research and Image-Guided Surgery of Breast Cancer, Breast Cancer Research and Treatment, 2004, 84(2):185-97.
Bouma et al., High-Resolution Imaging of the Human Esophagus and Stomach In Vivo Using Optical Coherence Tomography, Gastrointestinal Endoscopy, 2000, 51(4):1467-474.
Casaubieilh et al., Optical Fibre Fizeau-Based OCT, In Second European Workshop on Optical Fibre Sensors, 2004, International Society for Optics and Photonics, 5502:338-341.
Chinn et al., Optical Coherence Tomography Using a Frequency-Tunable Optical Souice, Optics Letters, 1997, 22 (5):340-342.
Fercher et al., Measurement of Intraocular Distances by Backscattering Spectral Interferometry, Optics Communications, 1995, 117(1-2):43-48.
Gonella et al., Diffusion Behavior of Transition Metals in Field-Assisted Ion-Exchanged Glasses, Solid State Ionics, 2006, 177(35-36):3151-3155.
Huang et al., Optical Coherence Tomography, Science, 1991, 254(5035):1178-1181.
Jang et al., In Vivo Characterization of Coronary Atherosclerotic Plaque by Use of Optical Coherence Tomography, Circulation, 2005, 111(12):1551-1555.
Mao et al., Graded-Index Fiber Lens Proposed for Ultrasmall Probes Used in Biomedical Imaging, Applied Optics, 2007, 46(23):5887-5894.
Mao et al., Fiber Lenses for Ultra-Small Probes Used in Optical Coherent Tomography, Journal of Biomedical Science and Engineering, 2010, 3:27-34.
Park et al., Low Reflectance Internal Mirrors, Conference Proceedings LEOS'96 9th Annual Meeting IEEE Lasers and Electro-Optics Society, Boston, MA, USA, 1996, pp. 178-179, vol. 2, doi: 10.1109/LEOS.1996.571610.
Ramaswamy et al., Ion-Exchanged Glass Waveguides: A Review, Journal of Lightwave Technology, 1988, 6(6):984-1002.
Sharma et al., Common-Path Optical Coherence Tomography with Side-Viewing Bare Fiber Probe for Endoscopic Optical Coherence Tomography, Review of Scientific Instruments, 2007, 78(11):113102, 4 pages.
Singh et al., Common Path Side Viewing Monolithic Ball Lens Probe for Optical Coherence Tomography, STM, 2015, 7(1):29-33.
Tearney et al., Optical Biopsy in Human Urologic Tissue Using Optical Coherence Tomography, The Journal of Urology, 1997, 157(5):1915-1919.
Villiger et al., Artifacts in Polarization-Sensitive OCT Caused by Polarization Mode Dispersion, Optics Letters, 2013, 38(6):923-925.
Wojtkowski et al., Ultrahigh-Resolution, High-Speed, Fourier Domain Optical Coherence Tomography and Methods for Dispersion Compensation, Optics Express, 2004, 12(11):2404-2422.
Zhang et al., A Surface Topology and Motion Compensation System for Microsurgery Guidance and Intervention Based on Common-Path Optical Coherence Tomography, IEEE Transactions on Biomedical Engineering, 2009, 56(9):2318-2321.
Zhang et al., Common-Path Low-Coherence Interferometry Fiber-Optic Sensor Guided Microincision, Journal of Biomedical Optics, 2011, 16(9):095003, 4 pages.
PCT International Search Report and Written Opinion, PCT/US2017/040701, dated Sep. 15, 2017, 13 pages.
European Patent Office, Extended European Search Report, Application No. 17824796.1, dated Feb. 21, 2020, 8 pages.
Japan Patent Office, Notification of Reason for Refusal, Application No. 2019-500337, dated Apr. 13, 2021, 10 pages.
European Patent Office. Office Action for application 17824796.1. dated Aug. 2, 2021. 4 pages.
Japan Patent Office. Notification of Reason for Refusal. Application No. 2019-500337, dated Jan. 11, 2022. 9 pages. With translation.
Korean Intellectual Property Office. Notice of Preliminary Rejection for application 10-2019-7003525. dated Oct. 29, 2021. 16 pages. With translation.
Japan Patent Office, Decision to Grant a Patent, Application No. 2019-500337, dated Jun. 24, 2022, 5 pages.
Korean Intellectual Property Office, Request for the Submission of an Opinion, Application No. 10-2019-7003525, dated Jul. 29, 2022, 13 pages.

* cited by examiner

SYSTEMS AND METHODS FOR AN ACTIVELY CONTROLLED OPTICAL IMAGING DEVICE

CROSS REFERENCE TO RELATED APPLICATIONS

The present application disclosure is a U.S. National Stage of PCT Application No. PCT/US2017/040701 filed on Jul. 5, 2017 which is based on, claims priority to, and incorporates herein by reference in their entirety, U.S. Provisional Patent Application No. 62/358,525, filed Jul. 5, 2016, and entitled "Apparatus and Methods for Common Path Optical Coherence Tomography", and U.S. Provisional Patent Application No. 62/516,853, filed Jun. 8, 2017, and also entitled "Apparatus and Methods for Common Path Optical Coherence Tomography".

STATEMENT REGARDING FEDERALLY SPONSORED RESEARCH

Not Applicable.

BACKGROUND

The present disclosure relates to imaging apparatus and device, and more particularly to exemplary embodiments of an optical coherence tomography (OCT) imaging system.

Since its first demonstration, optical coherence tomography (OCT) and its variants such as Endoscopic optical coherence tomography (EOCT) have rapidly advanced and found wide spread applications in medical imaging. EOCT is currently used as a diagnostic tool in coronary artery, esophagus, nasal cavity and prostate gland. EOCT has also been used for surgical guidance in ophthalmology and breast cancer.

Different forms of OCT such as time domain optical coherence tomography, spectrometer based Fourier domain optical coherence tomography and swept source based Fourier domain optical coherence tomography have been demonstrated. One thing which is common between all these OCT techniques is that a reference signal is required to reproduce the sample axial structure. In standard OCT systems, reference signal is generated using a Michelson interferometer based configuration and a mirror is used as reference surface. Michelson interferometer based schemes are regularly used in bench-top systems but it comes with several challenges in EOCT. First, majority of endoscopic probes use glass based optical fibers for signal guidance and in order to avoid material dispersion, length of optical fibers used in sample and reference arm should be closely matched. Second, endoscopic probes use external rotational devices to obtain circumferential images of the tissue and such fiber movements along with bending and stretching change the polarization state of the sample light. A mismatch in sample and signal polarization states leads to axial point spread function broadening and thus reducing the axial resolution and signal to noise ratio.

Issues related to separate reference arm in OCT are well known and different designs have been proposed to place reference surface close to the sample such that reference and sample signals travel the same material before reaching the detector. Such probes form a special class of probes called common path probes. Front viewing common path probes have been used in micro-incision guidance where reflection from cleaved fiber glass air interface was used as reference signal. Single mode fiber based circumferential scanning side viewing common path probes have been demonstrated where side surface of the fiber generates reference signal. Such probes lack control over working distance or focal distance from tip of the probe and have limited applications. In order to better control the focal properties, gradient index (GRIN) fiber based probes were purposed. In GRIN fiber based common path probes a single mode fiber is spliced to a coreless fiber followed by GRIN fiber and reflection from GRIN fiber air interface is used as reference signal. Such probes provide better control over the focal properties, however, back coupling of the reference signal and focal distance are interdependent and changing one will affect the other. Similar monolithic ball lens based probes have been demonstrated where reflection generated from the ball lens surface is used as reference signal, yet this design also shares the same problems with GRIN fiber based probes. Use of GRIN fiber and ball lens common path probes also require a separate reflector for circumferential imaging which further complicates the design. Ball lens non common path probe design eliminate the need of a separate reflector by polishing ball lens at an angle such that sample signal reflects from the polished surface because of total internal reflection. Accordingly, a need exists for a probe which does not require a separate reflector for circumferential scanning and reference power can set independently without affecting the focusing properties of the probe. A need further exists for a relative inexpensive design for a common path OCT probe where reference signal and focal distance can be set independent of one another.

BRIEF SUMMARY

In an aspect, the present disclosure provides a common-path optical waveguide probe. The common-path optical waveguide probe includes an optical waveguide, a lens, and a reference reflector. The optical waveguide includes a proximal end and a distal end. The lens is coupled to the distal end. The reference reflector is positioned between the optical waveguide and the lens.

In another aspect, the present disclosure provides a catheter. The catheter includes a common-path optical waveguide probe and a sheath. The common-path optical waveguide probe is as described in any aspect herein. The sheath is configured to receive the common-path optical waveguide probe.

In a further aspect, the present disclosure provides an optical coherence tomography (OCT) system. The OCT system includes an OCT light source, an OCT detector, a common-path optical waveguide probe or a catheter, a circulator, and an OCT controller. The common-path optical waveguide probe or the catheter are as described in any aspect herein. The circulator is coupled to the OCT light source, the OCT detector, and the common-path optical waveguide probe. The circulator is configured to direct light from the OCT light source to the common-path optical waveguide probe and from the common-path optical waveguide probe to the OCT detector. The OCT controller is couple to the OCT detector and configured to provide an OCT signal output representative of an OCT signal measured at the OCT detector.

In yet another aspect, the present disclosure provide a method of making a common-path optical waveguide probe. The method includes: splicing a first end of first optical waveguide and a second end of a second optical waveguide, wherein at least one of the first end and the second end has a reference reflector precursor positioned at a surface undergoing the splicing, thereby providing a reference reflector between the first optical waveguide and the second optical waveguide; and forming or attaching a lens to an opposite end of the first optical waveguide that is opposite the first end.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

Lengths and distances described herein are described in terms of optical path length lengths and distances, unless the context clearly dictates otherwise. Accordingly, light traveling along a coiled optical fiber travels a distance that is equal to the uncoiled length of the optical fiber, not the physical distance between the input and output of the optical fiber.

Figure 1:
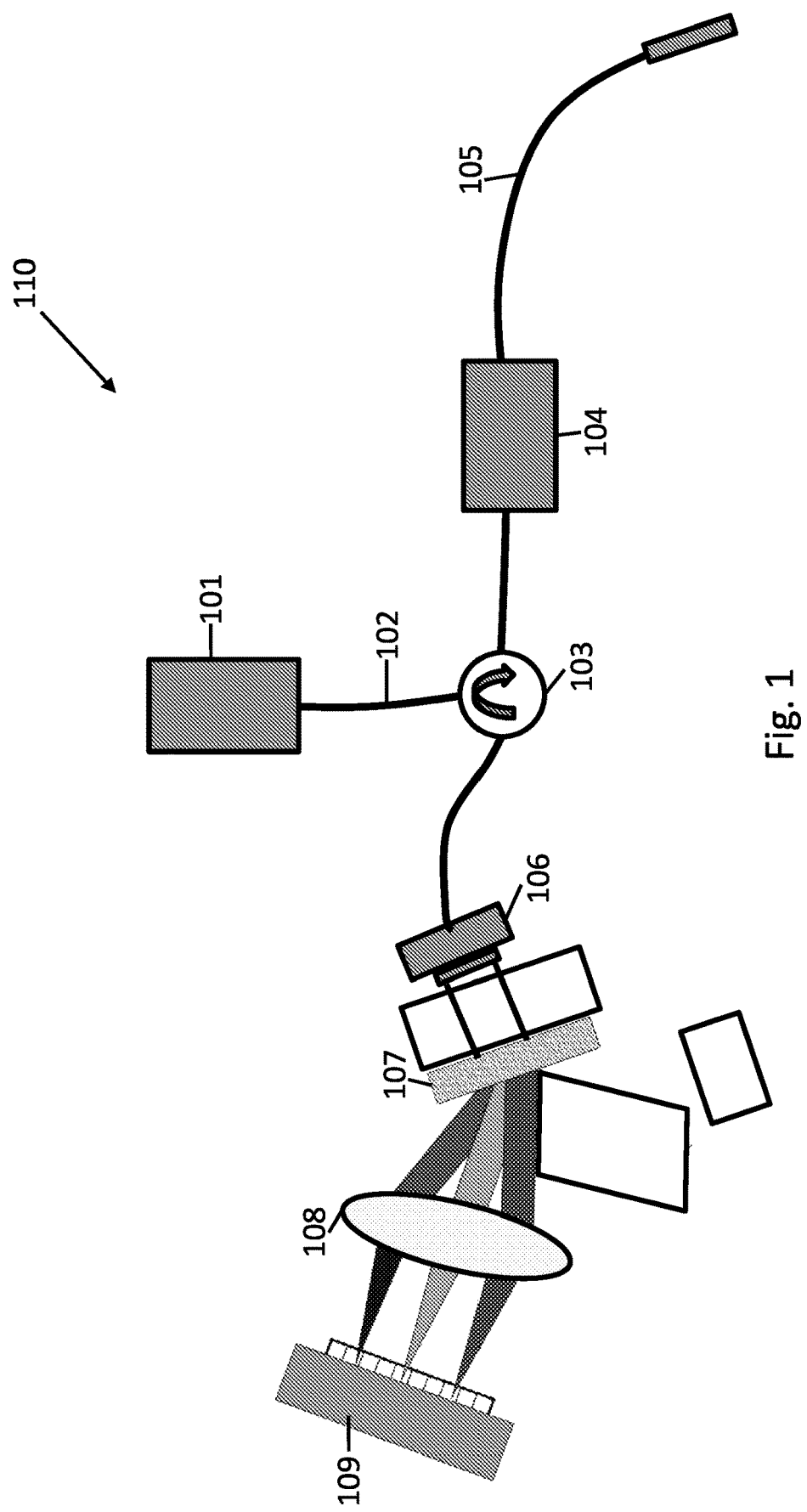
FIG. 1 is a schematic of a system, in accordance with an aspect of the present disclosure.

Referring to FIG. 1, an exemplary schematic of a spectral-domain OCT system 110 is illustrated. This system 110 can be used with the common-path optical waveguide probe 305 described elsewhere herein. Light emitted by a broadband light source 101 is coupled to a single mode fiber 102 and subsequently directed using a circulator 103 toward a rotary junction 104. The rotary junction 104 couples the light to a probe 105. Reference and sample light travel from the probe 105, through the rotary junction 104 and circulator 103 to the spectrometer, which in this case consists of a collimator 106, a grating 107, a spectrometer lens 108, and a linear array camera 109.

Figure 2A:
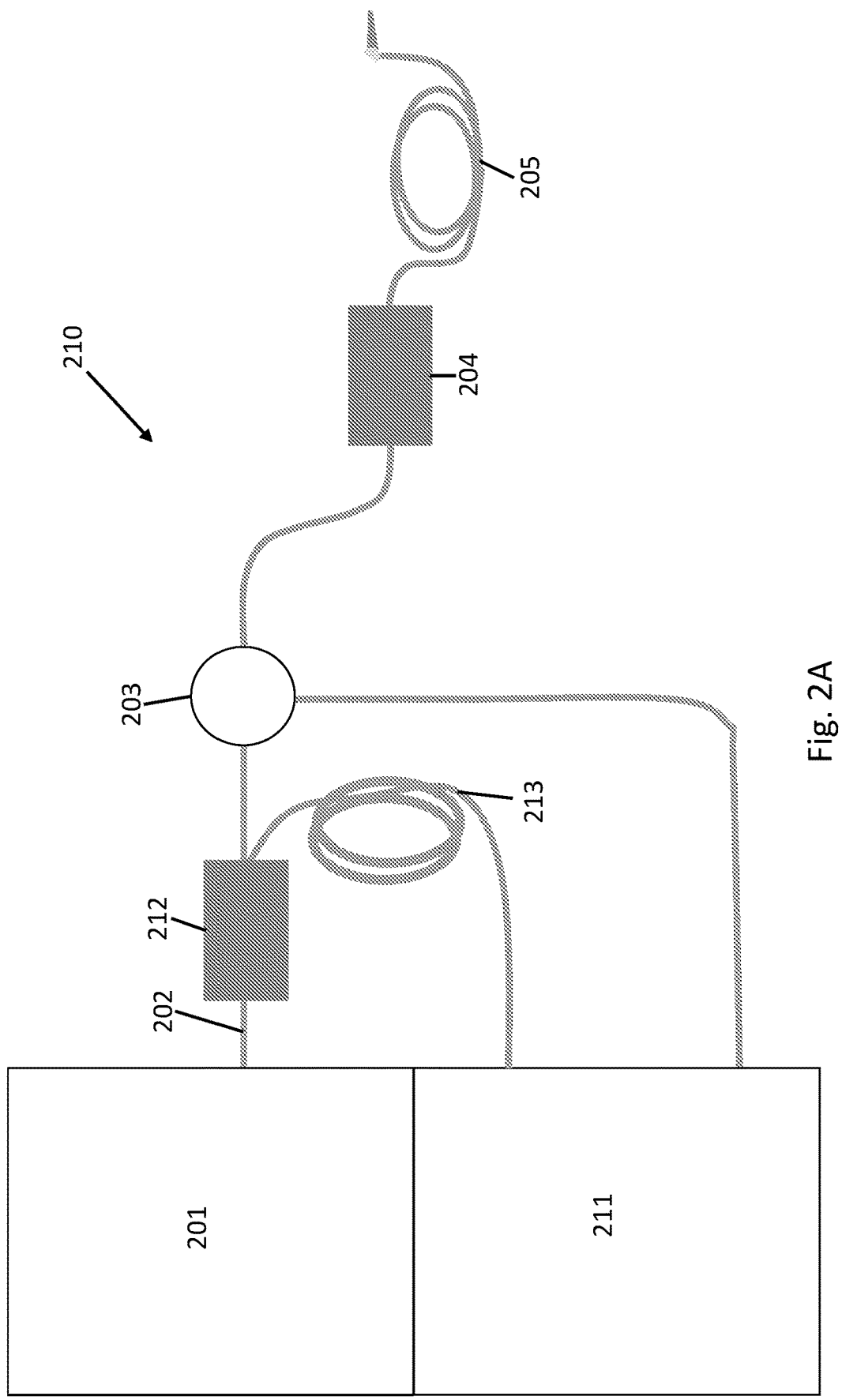
FIG. 2A is a schematic of a system, in accordance with an aspect of the present disclosure.
Figure 2B:
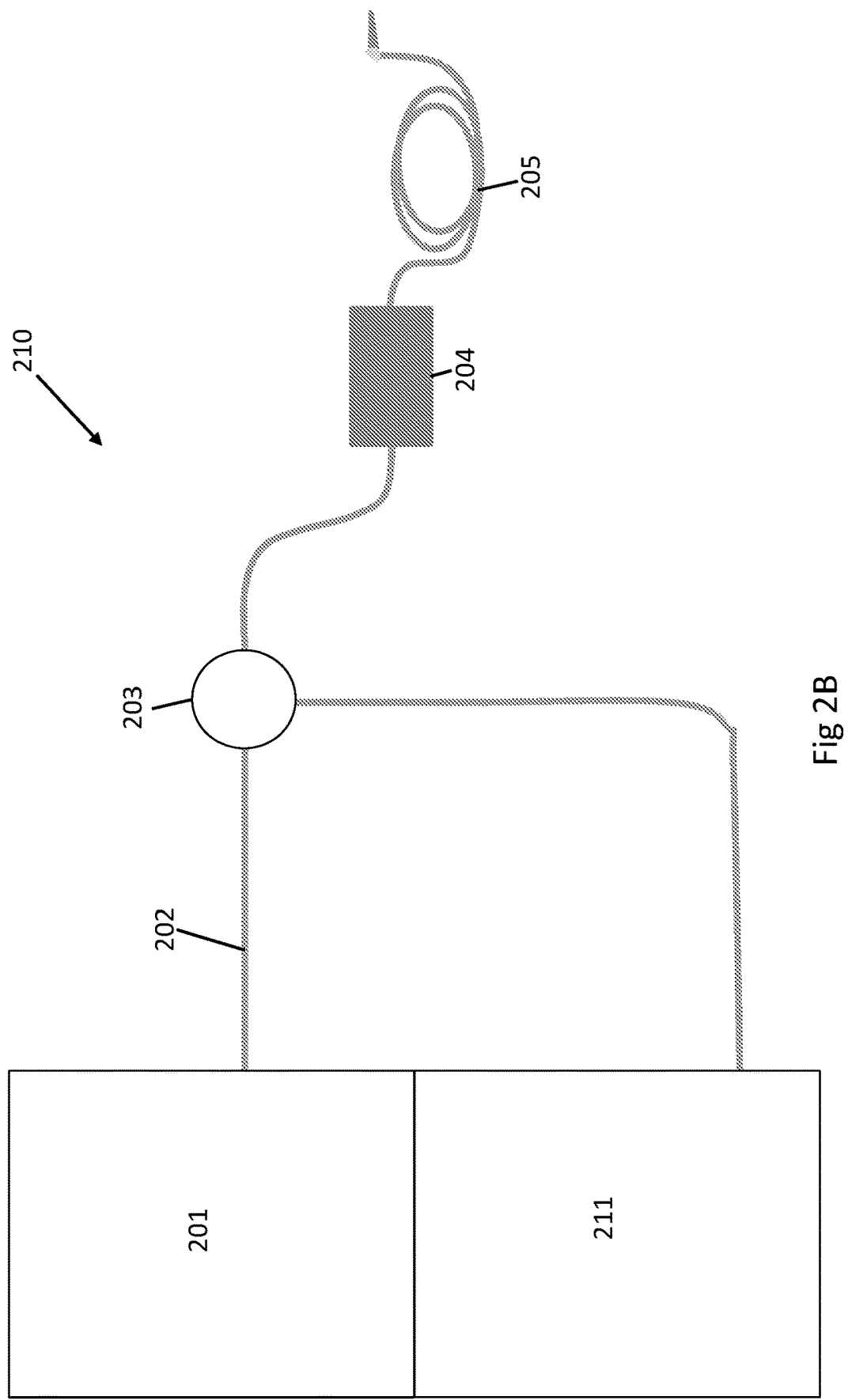
FIG. 2B is a schematic of a system, in accordance with an aspect of the present disclosure.

Referring to FIGS. 2A and 2B, two exemplary schematics of swept-source OCT or optical frequency-domain imaging (OFDI) systems 210 are illustrated. These systems 210 can be used with the common-path optical waveguide probe 305 described elsewhere herein. Light emitted by a broadband swept-source laser 201 is coupled to a single mode fiber 202 and subsequently directed using a circulator 203 toward a rotary junction 204. The rotary junction 204 couples the light to a probe 205. Reference and sample light travel from the probe 205, through the rotary junction 204 and circulator 203 to one channel of a balanced photodetector 211. In FIG. 2A, the light passing along the single-mode fiber 202 encounters a fiber coupler 212 (described generically elsewhere as a beamsplitter) which splits off a portion of the light and transmits that portion along a reference optical fiber 213 into the other channel of the balanced photodetector 211. In FIG. 2A, the fiber coupler 212 and the reference optical fiber 213 are omitted and only the one channel of the balanced photodetector 211 is used. When balanced detection is used, common mode noise can be reduced and, after subtracting signals of the two channels, DC spectral offset can be canceled.

Figure 2C:
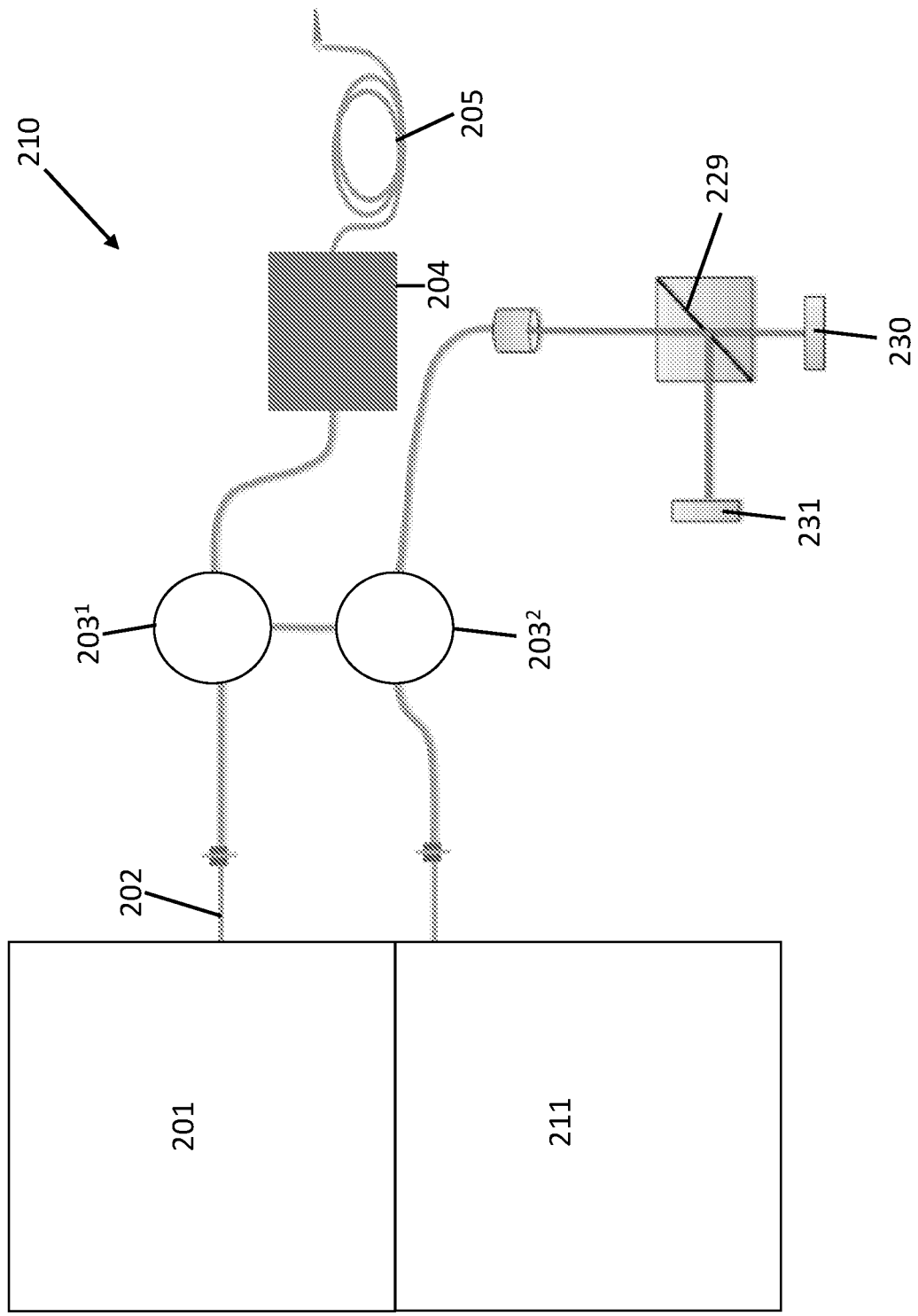
FIG. 2C is a schematic of a system, in accordance with an aspect of the present disclosure.

Referring to FIG. 2C, a third exemplary schematic of a swept-source OCT or OFDI system 210 is illustrated. This system 210 can be used with the common-path optical waveguide probe 305 described elsewhere herein. The function is similar to the function of the system 210 illustrated in FIG. 2B, but instead of a single circulator 203, the system includes a first circulator $203^1$ positioned and functioning like shown and described in FIG. 2B and a second circulator $203^2$ positioned between the first circulator $203^1$ and the balanced photodetector 211. The second circulator $203^2$ sends the signal received from the first circulator $203^1$ to a Michaelson interferometer, which includes a beamsplitter 229, a first mirror 230, and a second mirror 231. The signals reflected from the first mirror and the second mirror are coupled back to the second circulator $203^2$, which directs the combined signal to the detector 211. Varying one of the path lengths (in the illustrated cases, the path length of the second mirror 231) can provide a shift in the image window. In conventional OCT systems with separate sample and reference arms, path length differences can be accounted for by lengthening or shortening the reference arm. In the present system 210, the path length differences cannot be set to zero. For instance, with the designs described below placed in an 800 µm outer diameter sheath for imaging, the minimum distance between the sample and the reference reflector is 780 µm. Thus, the sample image cannot be placed within the first 780 µm of the imaging depth range. If the imaging depth is much greater than the distance between the reference surface and the outer surface of the sheath, this is not critical, but in some cases, such as balloon- or capsule-based gastrointestinal imagine applications where the sample is many millimeters away from the center of the probe, this is not suitable. The system 210 shown in FIG. 2C is usable to recover the imaging depth in these cases by adjusting one of the path lengths of the Michaelson interferometer. It should be appreciated that the system 210 shown in FIG. 2C can be used with any common path length interferometry, not just those utilizing the probes described herein.

In each of FIGS. 1, 2A, 2B, and 2C, the signals that are directed can include a reference signal and a sample signal, as described below with respect to the in-line reference reflector 318 within the common-path optical waveguide probe 305.

The system 110, 210 can include a controller configured to control the various light sources and/or the detectors. In some cases, the controller can be a computer programmed to acquire signals and execute the methods described herein.

The system 110, 210 can include a motor, such as a micro-motor, for circumferential scanning. The system 110, 210 can include a two-dimensional translation stage for translating the probe and/or the probe tip.

The system 110, 210 can include a second imaging modality, such as fluorescence, autofluorescence, Raman, or other spectroscopy. For these cases, the system 110, 210 can include a second imaging modality light source and a second imaging modality detector.

The system 110, 210 can be configured for free space two-dimensional scanning. In these cases, the system 110, 210 can include two galvanometers used to steer the beam to scan across the sample.

Figure 3:
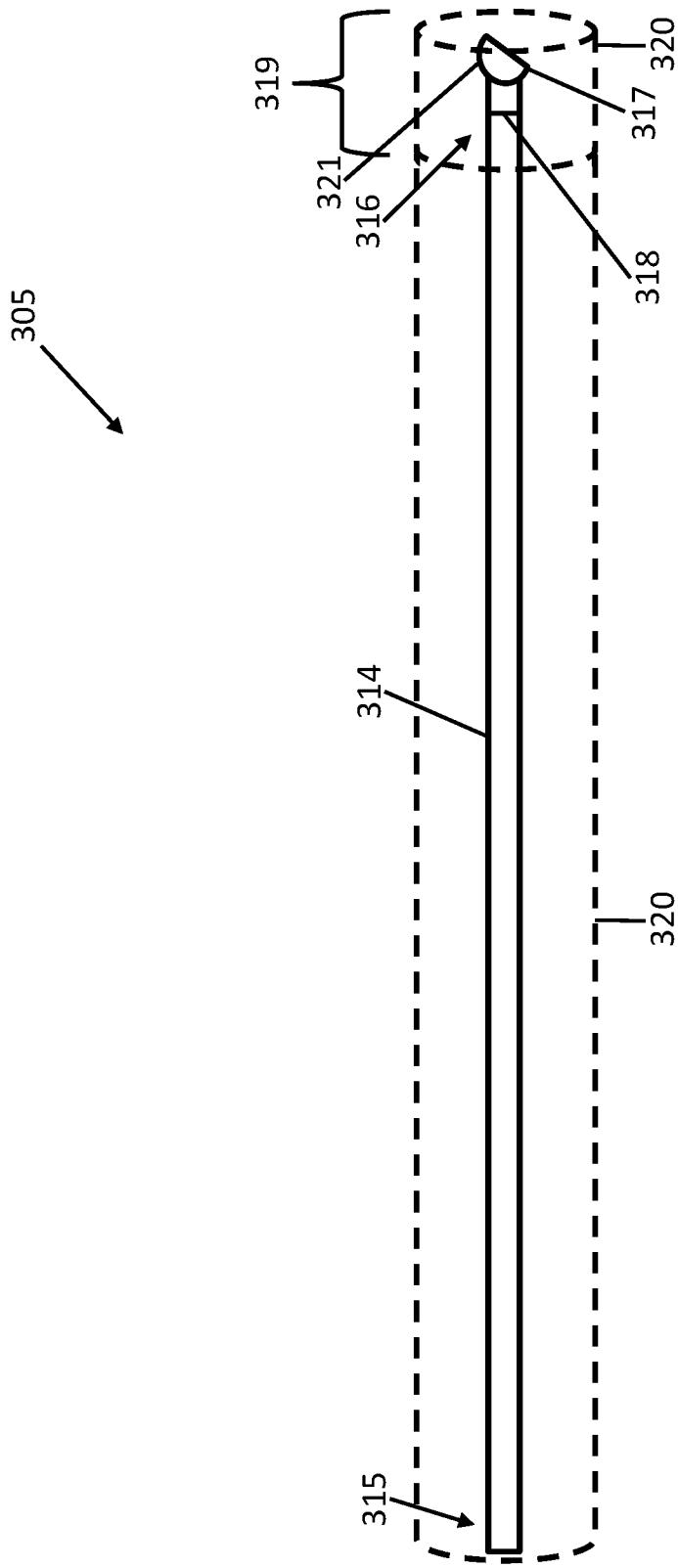
FIG. 3 is a schematic of a common-path optical waveguide probe, in accordance with an aspect of the present disclosure.

Referring to FIG. 3, a common-path optical waveguide probe 305 is illustrated. The probe 305 includes an optical waveguide 314 having a proximal end 315 and a distal end 316. A lens 317 is coupled to the distal end 316. A reference reflector 318 is positioned between the optical waveguide 314 and the lens 317. The distal end 316 includes a distal tip 319. The distal tip 317 can include the features of any of the distal tips shown below and illustrated in FIGS. 4A-6 and 10-11. The probe 305 and/or the distal tip 319 can optionally include a driveshaft 320. In some cases, the driveshaft 320 is a single driveshaft, but non-monolithic driveshafts are also contemplated. The optical waveguide 314, the reference reflector 318, and the lens 317 can be directly coupled to one another or can have intervening optics or spaces, as understood by a person having ordinary skill in the art. For example, the probe 305 can include a spacer (not illustrated) positioned between the optical waveguide 314 or the reference reflector 318 and the lens 317. The spacer can be configured for beam propagation.

The probe 305 is illustrated as linear, but the probe 305 can also be curved. In some cases, the probe 305 can be flexible. In some cases, the probe 305 can be rigid.

The optical waveguide 314 can have a waveguide length of 1000 m or less, 10 m or less, or between 1 cm and 5 m.

The lens 317 can include an emission surface 321 from which the light emanates. A reference reflector-emission surface distance between the reference reflector 318 and the emission surface 321 can be 1 m or less, 10 cm or less, or 1 cm or less.

The probe 305 can be configured to have a ratio of waveguide length to reference reflector-emission surface distance of at least 100:1, including but not limited to, a ratio of at least 1000:1, at least 10,000:1, at least 100,000:1, or at least 1,000,000,000:1.

The reference reflector 318 can be composed of materials known to have controllable selective reflectivity, including but not limited to, a metal, a dielectric material, or a non-metal, non-dielectric material having an index of refraction that is different from an optical waveguide index of refraction of the optical waveguide by an amount sufficient to cause a predictable selective reflectance. The metal can be any reflective metal, including but not limited to, gold, silver, aluminum, platinum, and combinations thereof. The dielectric material can be a dielectric material known to those having ordinary skill in the art, including but not limited to, zinc sulfide, titanium dioxide, magnesium fluoride, silicon dioxide and combinations thereof.

The reference reflector 318 can be a film. A reference reflector film can have a thickness of between 1 pm and 1 mm, between 1 pm and 10 µm, or between 1 pm and 1 µm.

In some cases, the reference reflector 318 is a metal film. In some cases, the reference reflector 318 is a dielectric film. In some cases, the reference reflector 318 is a non-metal, non-dielectric material film.

In some cases, the reference reflector 318 is not glass. In some cases, the reflectivity of the reference reflector 318 is not based on a difference between the indices of refraction of the reference reflector 318 and air. The reference reflector 318 is not the sheath of a catheter (which can often be glass) or a capsule for a capsule-based probe. The reference reflector 318 is not the surface of the lens 317.

The reference reflector 318 can be configured to selectively reflect between 0.000001% and 2.0% of the light, including but not limited to, between 0.00001% and 1.0% of the light, between 0.00005% and 0.5% of the light, between 0.0001% and 0.1% of the light, or between 0.0005% and 0.01% of the light.

In some cases, the reflectance of the reference reflector 318 can be tuned to a known light source having a known optical power, thereby providing a predictable optical power of the reflected light. In those cases, the reference reflector can be tuned to provide maximum sensitivity by taking into account the various sources of noise, such as thermal noise, shot noise, and relative intensity noise, among others. The reference reflector 318 can be tuned to a known light source having a known optical power to provide a predictable reflective optical power of between 1 μW and 10 mW, including but not limited to, a predictable reflective optical power of between 5 μW and 1 mW, between 10 μW and 100 μW, or between 20 μW and 40 μW.

The selective reflectivity of the reference reflector 318 can be tuned to the optical waveguide 314 alone, in which case the intensity measurements are made at the proximal end 315 of the optical waveguide 314, or for the system 110, 210 in its entirety, in which case the intensity measurements are made at the spectrometer or detector of the system 110, 210. The selective reflectivity of the reference reflector 318 can be described relative to light intensity emitted from a light source, relative to measured or estimated light intensity introduced into the proximal end 315 of the optical waveguide 314, or relative to measured or estimated light intensity within the optical waveguide 314 upon reaching the reference reflector 318. Estimated light intensities can be estimated by measuring an intensity of a light source and measuring intensity loss from equivalent optics to those within the system 110, 210 or the probe 305.

The selective reflectivity and/or the thickness of the reference reflector 318 can be tuned in a variety of ways. As one example, when splicing an optical fiber including a metal coated end surface to an optical fiber with no coating on an end surface, the operational parameters of the splicing can be varied to vary the selective reflectivity and/or the thickness of the resulting reference reflector 318. The temperature and timing of the splicing can be varied to adjust these properties. This process is discussed in greater detail below.

The lens 317 can take a variety of forms, including a ball lens, a spherical lens, an aspherical lens, a graded index (GRIN) fiber lens, an axicon, a diffractive lens, a meta lens, a phase manipulation lens that utilizes lensing with phase manipulation, or the like.

Figure 4A:
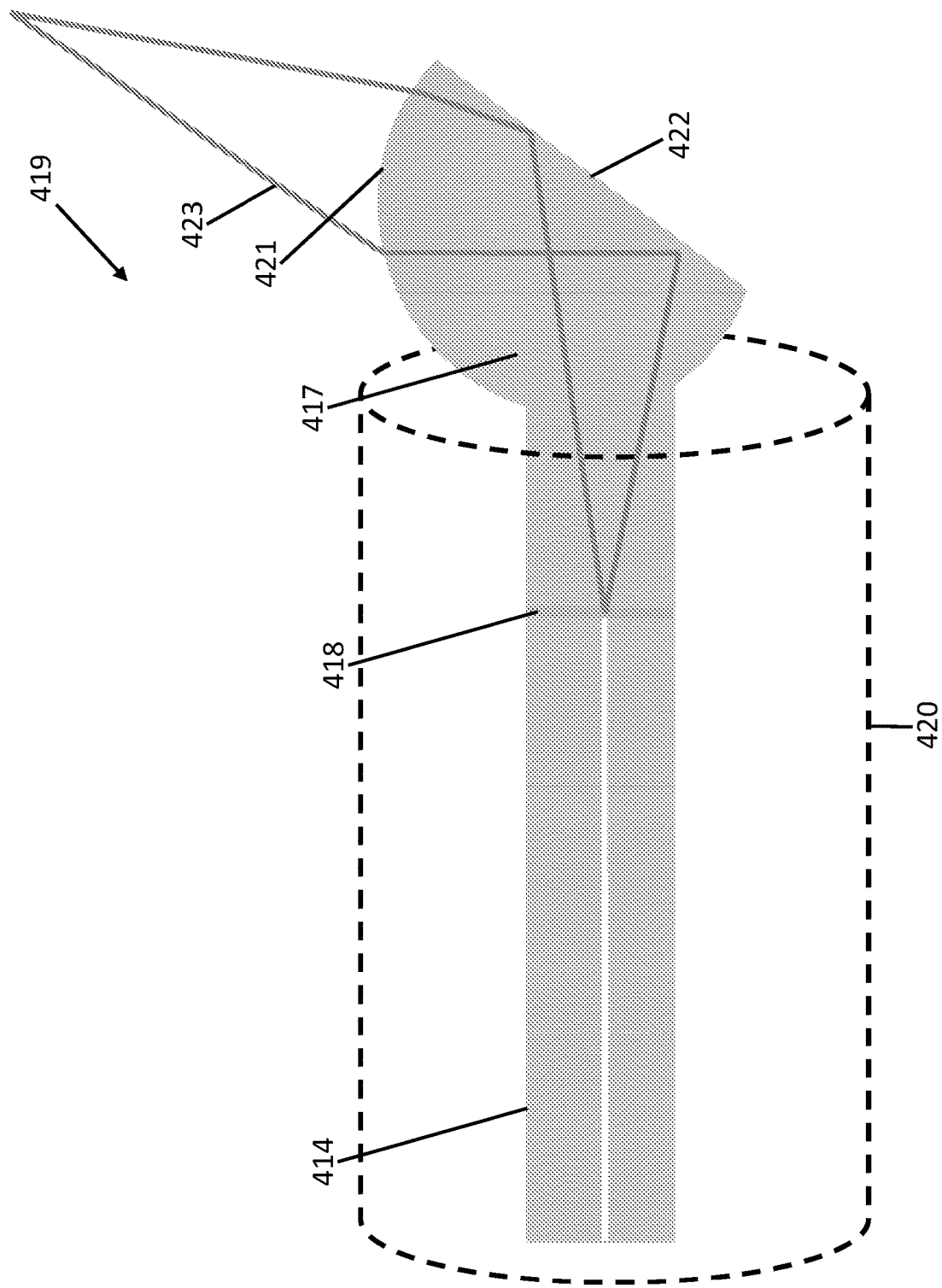
FIG. 4A is a schematic of a distal tip of a common-path optical waveguide probe, in accordance with an aspect of the present disclosure.

Referring to FIG. 4A, an exemplary distal tip 419 is illustrated. The distal tip 419 can include a portion of the optical waveguide 414, a reference reflector 418, and a lens 417 having an emission surface 421 and a reflective surface 422. The light 423 is illustrated emerging from the optical waveguide 414, passing through the reference reflector 418, diverging as it passes through the lens 417, reflecting off the reflective surface 422, and emerging from the emission surface 421. The distal tip 419 can optionally include a drive shaft 420. In this aspect, when the drive shaft 420 is present, all of the components of the distal tip 419 are contained within the drive shaft 420. The drive shaft 420 can include a window (not illustrated) through which the light 423 passes.

Figure 4B:
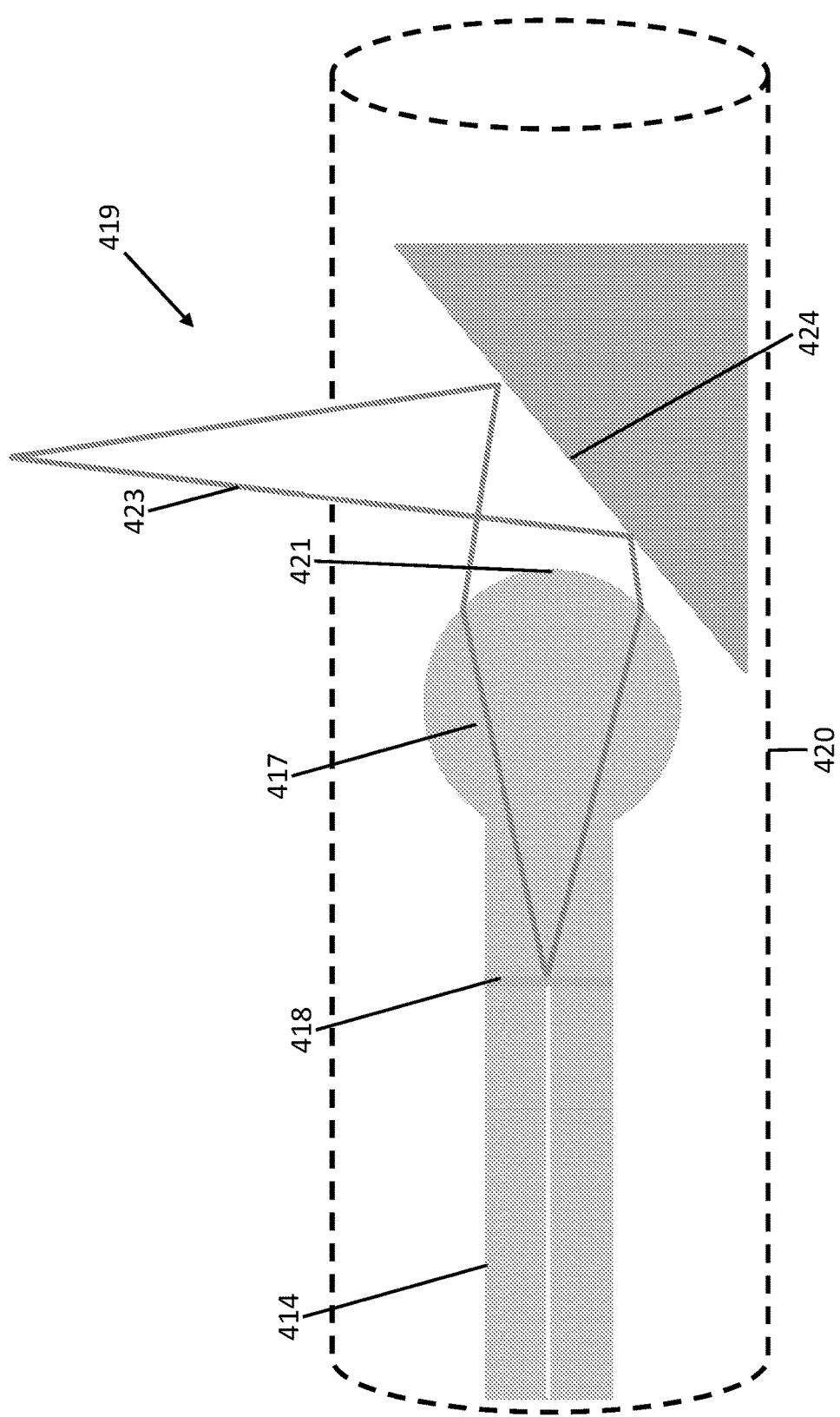
FIG. 4B is a schematic of a distal tip of a common-path optical waveguide probe, in accordance with an aspect of the present disclosure.

Referring to FIG. 4B, an exemplary distal tip 419 is illustrated. The parts are similar to the aspect illustrated in FIG. 4A, but instead of a reflective surface 422 on the lens 417, the distal tip 419 includes an external reflective surface 424. In this illustrated aspect, the light 423 emerges from the emission surface 421 of the lens 417 and is reflected off the external reflective surface 424.

Figure 5A:
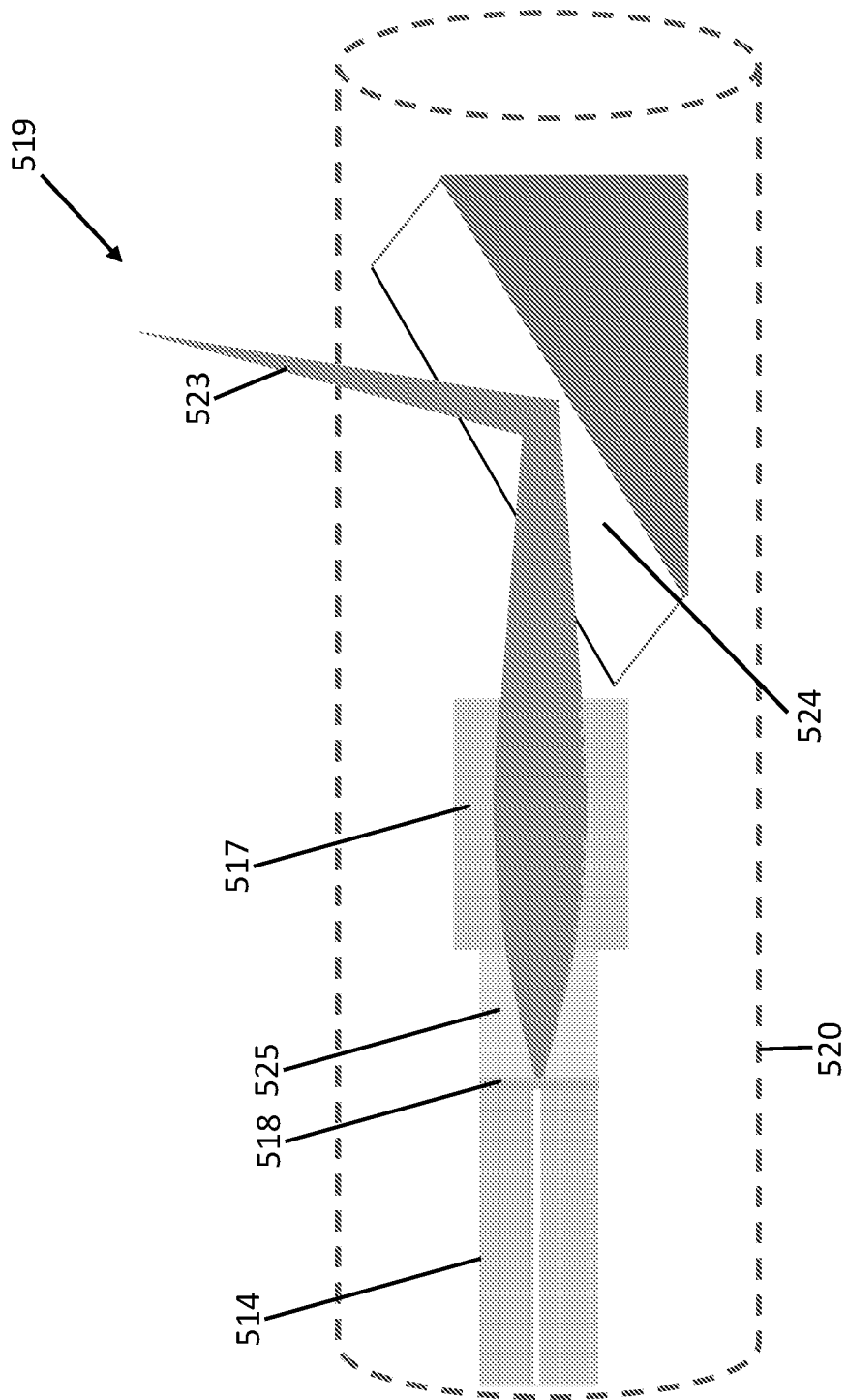
FIG. 5A is a schematic of a distal tip of a common-path optical waveguide probe, in accordance with an aspect of the present disclosure.

Referring to FIG. 5A, another exemplary distal tip 519 is illustrated. The distal tip can include a portion of the optical waveguide 514, a reference reflector 518, an expansion region 525, and lens 517, an external reflective surface 524, and an optional drive shaft 520. The lens 517 illustrated in FIG. 5 can be a graded index (GRIN) fiber lens. The expansion region 525 can be a coreless fiber. The light 523 emerges from the optical waveguide 514, passes through the reference reflector 518, expands in the expansion region 525, passes through and is focused by the lens, and reflects off the external reflective surface 524.

Figure 5B:
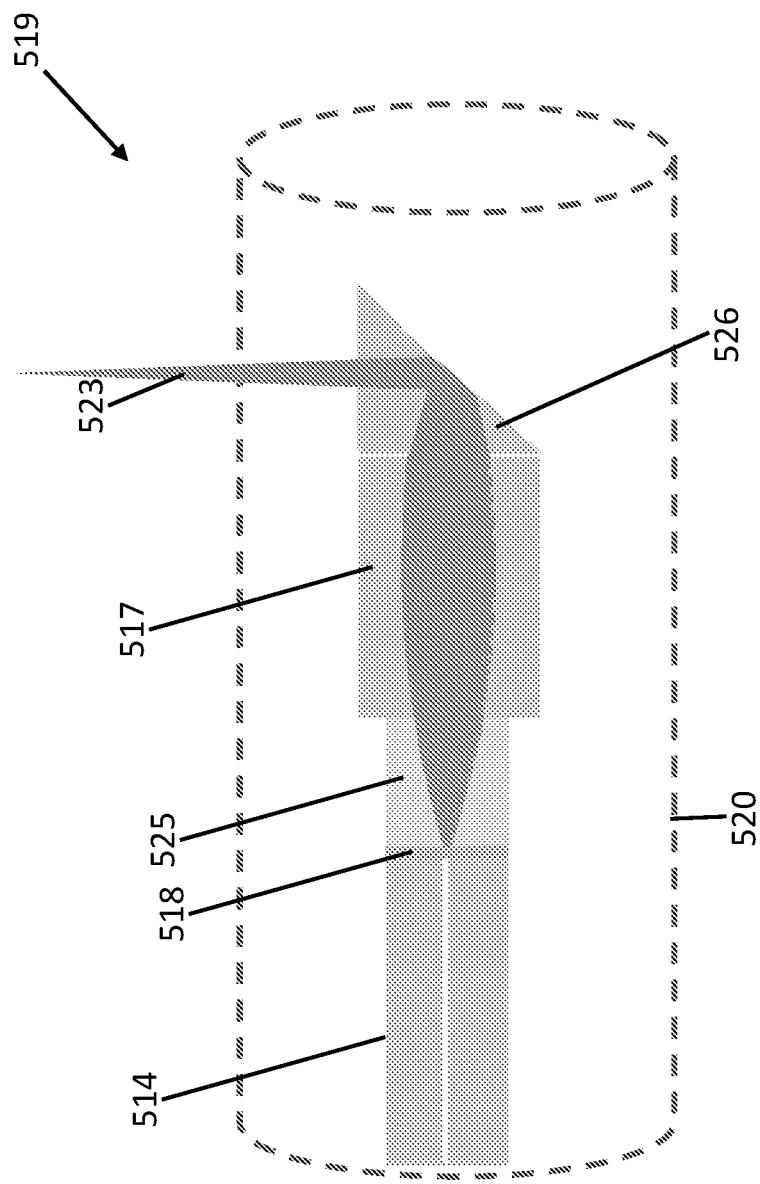
FIG. 5B is a schematic of a distal tip of a common-path optical waveguide probe, in accordance with an aspect of the present disclosure.

Referring to FIG. 5B, an exemplary distal tip 519 is illustrated. The parts are similar to the aspect illustrated in FIG. 5, but instead of an external reflective surface 524, a prism 526 directs the light 523 into the target. The lens 517 and prism 526 can be separate and distinct components or can be monolithic.

Figure 6:
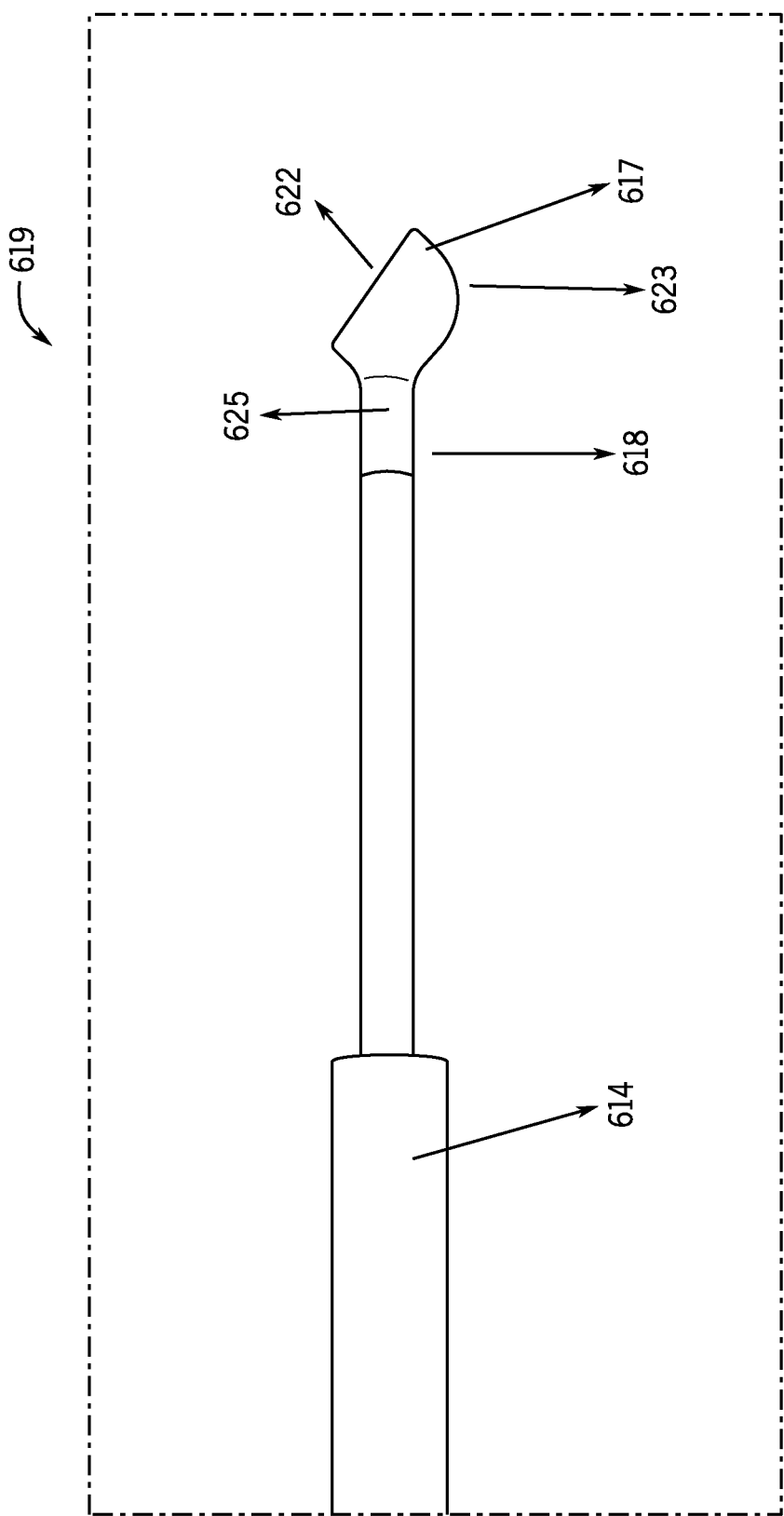
FIG. 6 is an image of a distal tip of a common-path optical waveguide probe, in accordance with an aspect of the present disclosure.

Referring to FIG. 6, an image of a distal tip 619 of a probe 605 with design principles similar to those shown in FIGS. 4A and 5A is shown. The distal tip 619 includes an optical waveguide 614 in the form of a single-mode optical fiber, a reference reflector 618 in the form of a thin gold layer, an expansion region 625 in the form of a coreless region, and a lens 617 in the form of a ball lens. The ball lens is polished to include a reflective surface 622 and the ball lens includes an emission surface 621.

Figure 7:
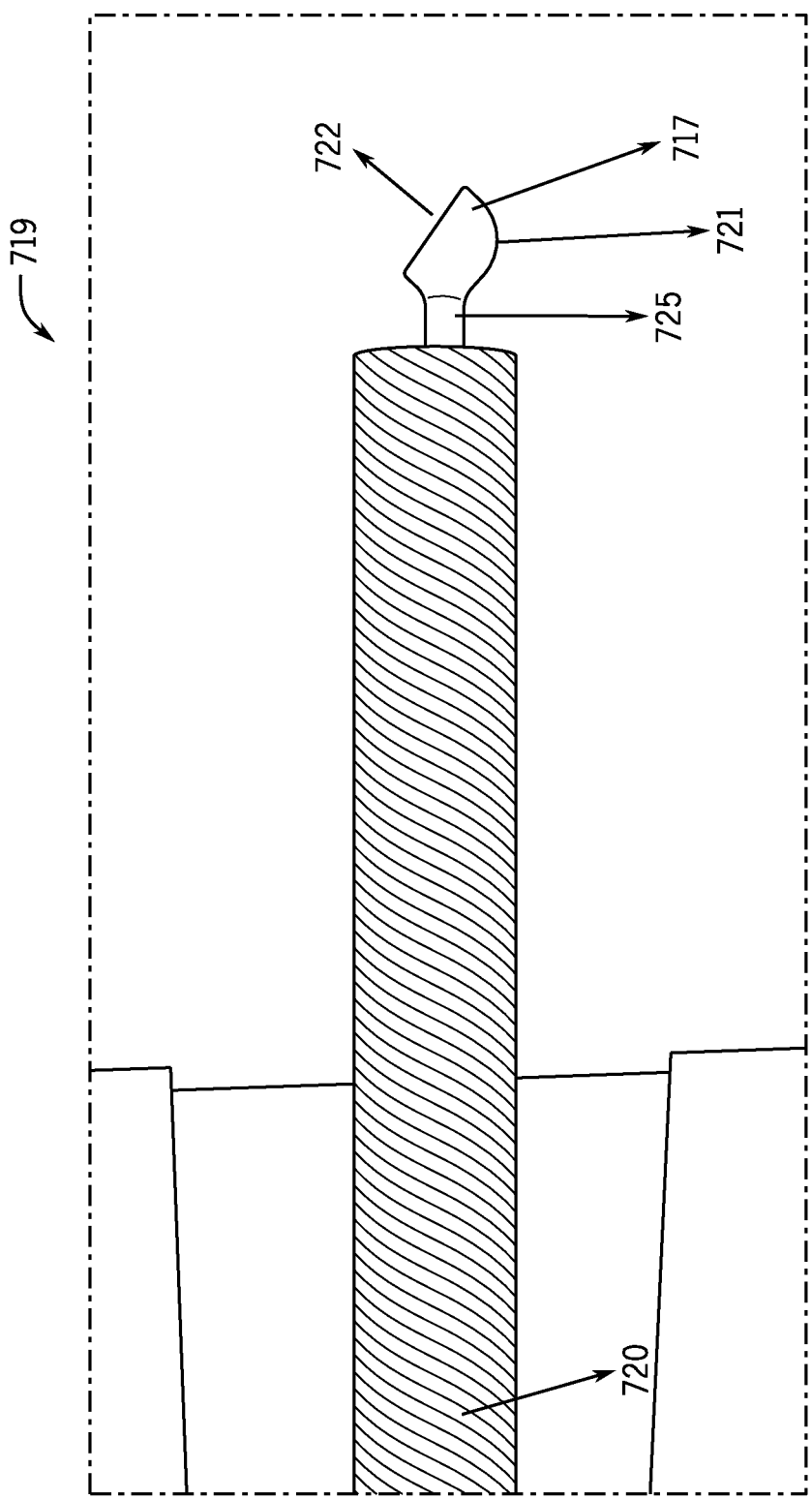
FIG. 7 is an image of a distal tip of a common-path optical waveguide probe, in accordance with an aspect of the present disclosure.

Referring to FIG. 7, an image of a distal tip 719 of a probe 705 with design principles similar to FIGS. 4A and 5A are shown. The distal tip 719 includes the drive shaft 720, which is covering much of the structure of the distal tip 719. The expansion region 725 in the form of a coreless region and the lens 717 in the form of a ball lens emerge from the drive shaft 720 and are visible. The ball lens is polished to include a reflective surface 722 and the ball lens includes an emission surface 721.

Figure 8:
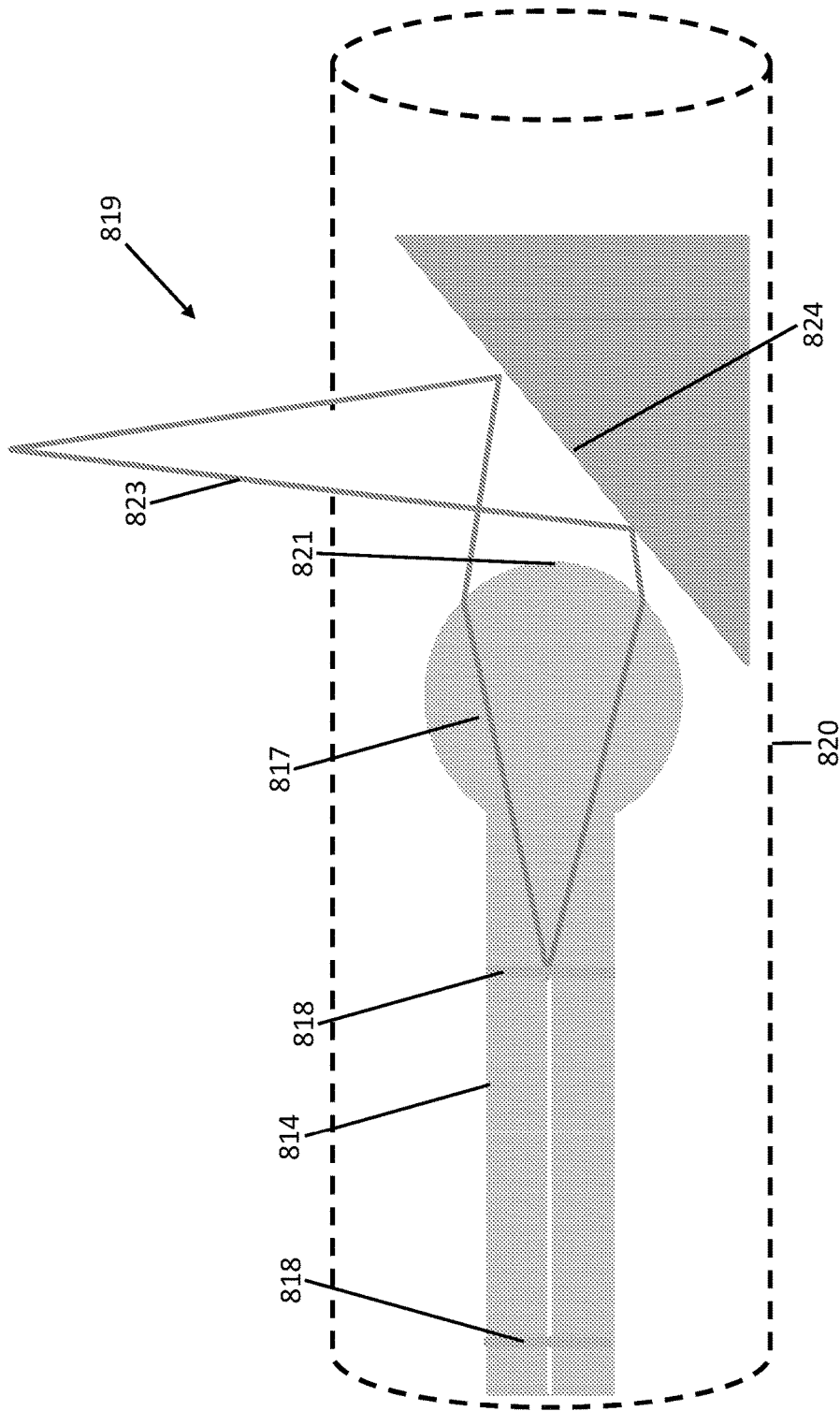
FIG. 8 is a schematic of a distal tip of a common-path optical waveguide probe, in accordance with an aspect of the present disclosure.

Referring to FIG. 8, in some cases, the probe 805 can have a distal tip 819 that includes more than one reference reflector 818, such as the illustrated aspect with two reference reflectors 818. The distal tip 819 includes the portion of the optical waveguide 814, the lens 817, the emission surface 821, the external reflective surface 824, and the optional drive shaft 820, as described above with respect to FIG. 5A.

Figure 9:
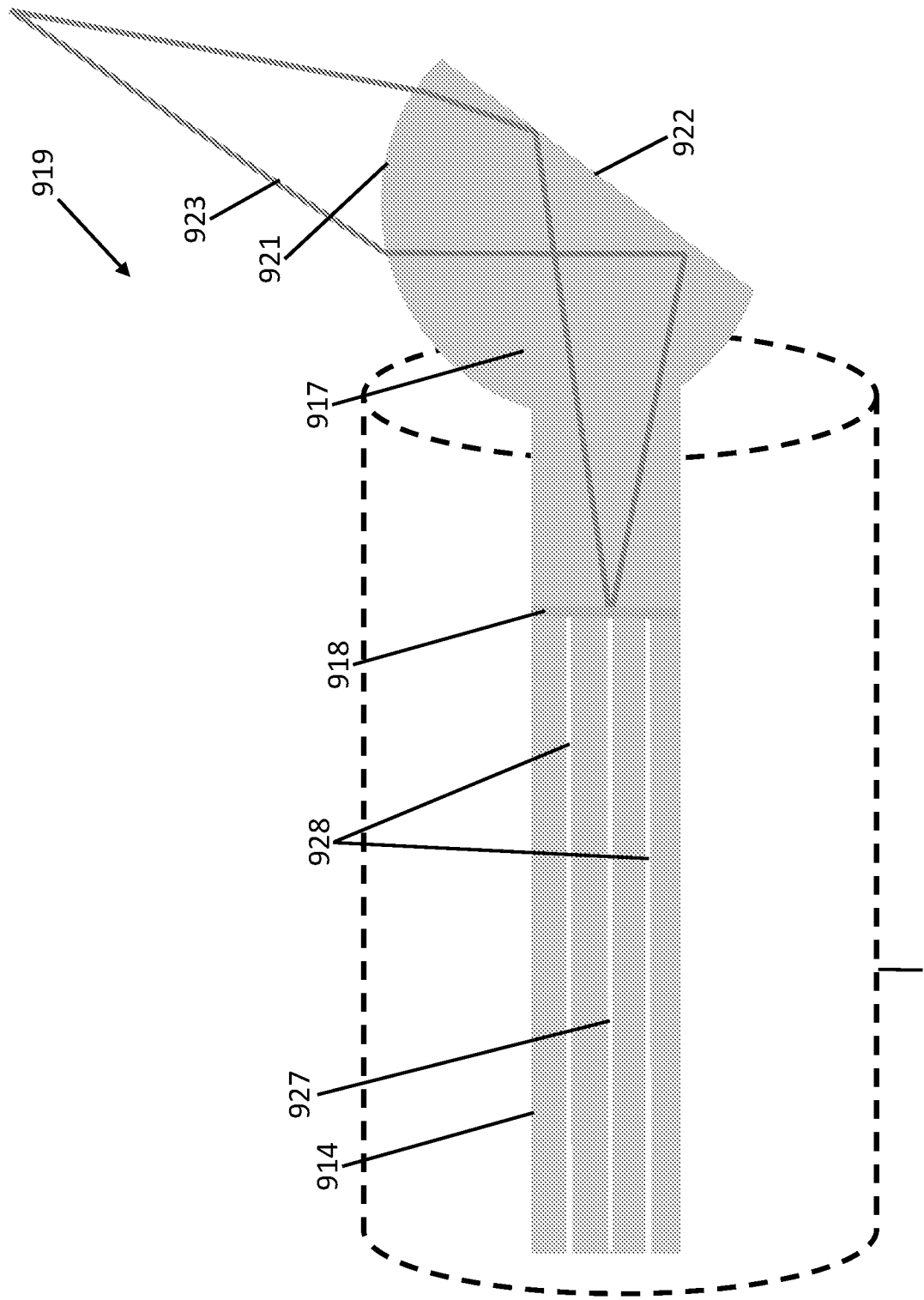
FIG. 9 is a schematic of a distal tip of a common-path optical waveguide probe, in accordance with an aspect of the present disclosure.

Referring to FIG. 9, in some cases, the probe 905 and the distal tip 919 can include an optical waveguide 914 in the form of a double clad fiber. The double clad fiber can include a core 927 and an inner cladding 928. The core 927 can be used to transmit an OCT signal. The inner cladding 928 can be used for delivery and detection of fluorescence, autofluorescence, Raman, or other spectroscopy signals. This arrangement can enable multi-modality imaging with an inline fiber mirror common path probe 905. The distal tip 919 includes the reference reflector 918, the lens 917, the reflective surface 922, the emission surface 921, and the optional drive shaft 920, as described above with respect to FIG. 4A.

In certain cases, the system 110, 210 and/or the probe 305 can be configured to have an axial resolution of better than 10 μm, better than 7.5 μm, better than 5 μm, better than 4 μm, better than 3 μm, better than 2 μm, or better than 1 μm.

In certain cases, the system 110, 210 and/or the probe 205 can be configured to have a lateral resolution of better than 50 μm, better than 40 μm, better than 35 μm, better than 32 μm, better than 30 μm, or better than 25 μm.

In certain cases, the system 110, 210 and/or the probe 305 can be configured to have a sensitivity of better than 80 dB, better than 90 dB, better than 100 dB, better than 105 dB, better than 110 dB, or better than 115 dB.

The system 110, 210 and/or the probe 305 can be configured to provide an image range of between 1 µm and 1 m.

In cases where the system 210 includes the Michaelson interferometers, the image range can be adjusted by between 1 µm and 1 m, including but not limited to, between 10 µm and 100 mm, between 100 µm and 50 mm, between 1 mm and 25 mm, or between 10 mm and 20 mm.

In certain cases, the target medium can be tissue, such as blood vessels, skin, gastrointestinal tissues, cardiovascular tissue, lung tissue, brain tissue, urologic tissues, gynecologic tissues, or the like.

In an aspect, the present disclosure provides a catheter. The catheter can include the common-path optical waveguide probe as described herein and a sheath configured to receive the probe. The catheter can be an endoscopic catheter.

In an aspect, the present disclosure provides a method of making a common-path optical waveguide probe, such as those described above. The method can include splicing a first end of a first optical waveguide and a second end of a second optical waveguide; and forming or attaching a lens to an opposite end of the first optical waveguide that is opposite the first end. At least one of the first end and the second end has a reference reflector or a reference reflector precursor positioned at a surface undergoing the splicing. The method can further include forming or positioning a reflective surface to direct light to a target medium.

The splicing can be any splicing method known to those having ordinary skill in the art, including but not limited to, laser splicing. One or more parameters of the splicing, such as the intensity and/or duration of the laser splicing, can be selected to provide a predetermined thickness or reflectivity of the reference reflector.

In one specific example, a coreless fiber having an end face coated with gold can be spliced with a single mode fiber. This splicing forms a gold surface at the interface of the single mode fiber and the coreless fiber. The splicing itself can affect the optical properties of the resulting reference reflector. The splicing can be laser splicing, where an initial pulse of laser light is used to splice the pieces together. Subsequent pulses of laser light can be used to change the optical properties of the reference reflector. Typically, in the case of a metal reference reflector, the subsequent pulses will reduce the reflectivity. This selective tuning can provide desired optical properties for the reference reflector, thereby giving a reference beam having the properties described above.

The forming or attaching a lens step can be done before or after the splicing and can be achieved in a variety of ways known to those having ordinary skill in the art. As one example, a lens can be optically contacted with the end of the spliced fiber. As another example, a ball lens can be formed by heating a coreless fiber and shaping the heated fiber into a ball lens.

The forming or positioning a reflective surface step can be done before or after the splicing or the forming or attaching lens step and can be achieved in a variety of ways known to those having ordinary skill in the art. As one example, a mirror can be positioned adjacent to the lens at an angle suitable for reflecting light into a target. As another example, when a ball lens or other lens is utilized, the lens can be polished to itself include a reflective surface. The polished reflective surface can be positioned at an angle relative to the optical waveguide that produce and angle of incidence for light that provides total internal reflection of the light.

Figure 10:
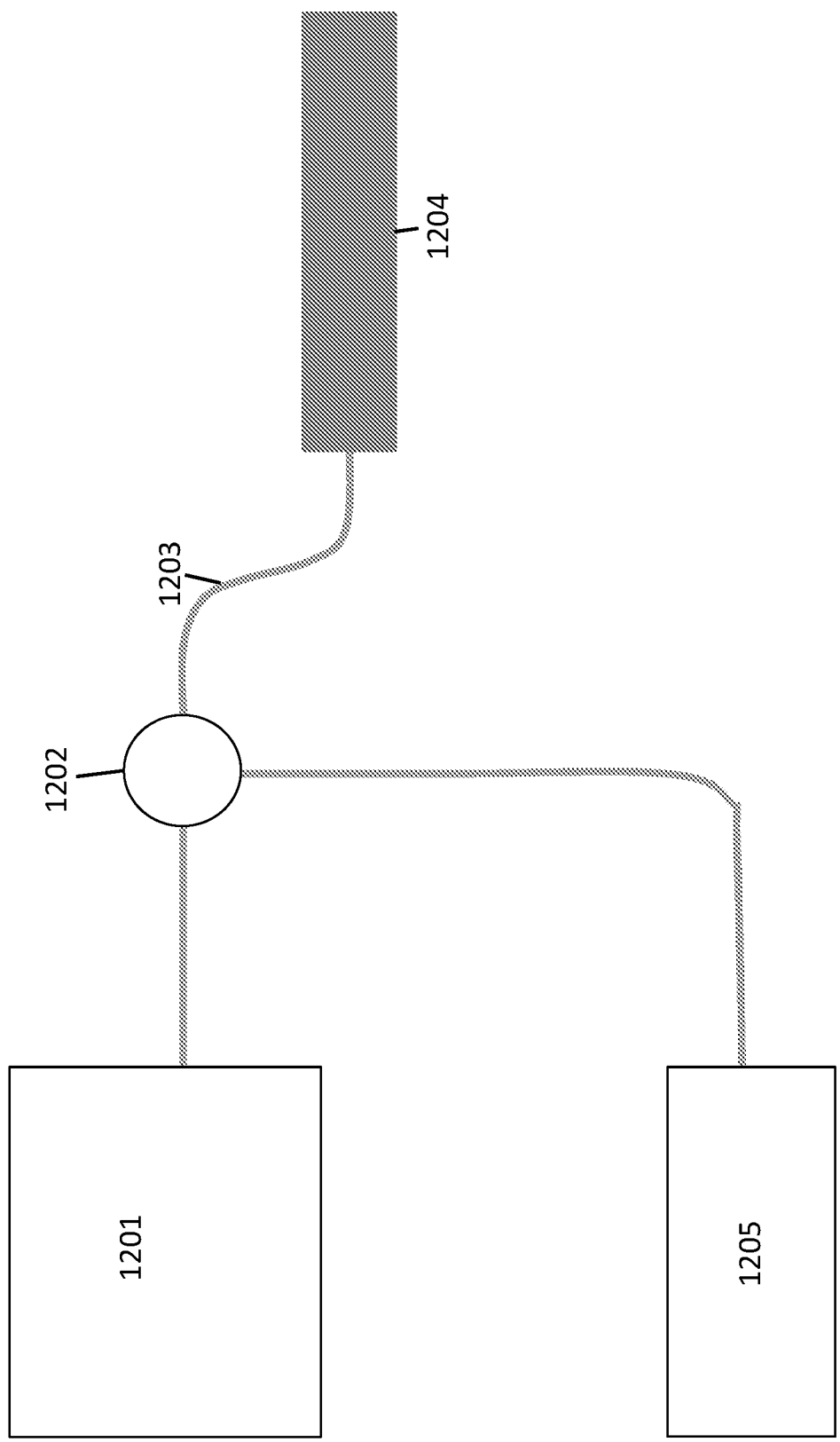
FIG. 10 is a schematic of a system for measuring reflectance of a reference reflector, in accordance with an aspect of the present disclosure.

Referring to FIG. 10, a system 1000 for measuring reflected reference power is shown. This system 1000 can be used to selectively tune a reflectivity of the reference reflector. The system 1000 includes a laser 1001 that is coupled to a circulator 1002, which send the light to a fiber that is undergoing a splicing such as described above. The splicer 1004, such as the laser splicer, is used to execute the splicing.

In certain aspects, the present disclosure provides a method of acquiring an OCT image. The method can use the systems or probes described herein. The method can include transmitting light through the probes described herein and into the target medium, scanning the probe across target medium, detecting a sample signal and a reference signal, and generating an image from the sample signal and the reference signal.

The methods can be performed by a spectral-domain system, using a low-coherence light source that emits a broad spectrum of light, acquiring a spectrum fringe signal by spreading the spectrum in one dimension, then collecting A-scan signal through a line-scan camera and subsequently digitizing the analog signal using a frame grabber. The methods can be performed with a swept-source or OFDI system by delivering a series of narrow linewidth light into the probe, receiving time-encoded fringe signal through photodetectors, then digitizing the signal via an analog-to-digital converter card. Balance detection can be used to reduce common mode noise. Polarization-diversity detection can be used to reduce the effect of polarization mode dispersion. The probes described herein are suitable for use in all of the aforementioned OCT imaging schemes and others known to those having ordinary skill in the art.

The systems 110, 210, probes 305, and methods described herein can be used for any processes utilizing catheters, including flexible catheters. Such processes include in vivo imaging, such as in vivo cardiology or gastrointestinal tract imaging.

The probe 305 can be used for spectrometer-based Fourier domain or spectral-domain OCT measurements.

EXAMPLES

The following examples set forth, in detail, ways in which the optical system 110, 210 and/or the common-path optical waveguide probe 305 may be used or implemented, and will enable one of skill in the art to more readily understand the principles thereof. The following examples are presented by way of illustration and are not meant to be limiting in any way.

Example 1

Figure 11:
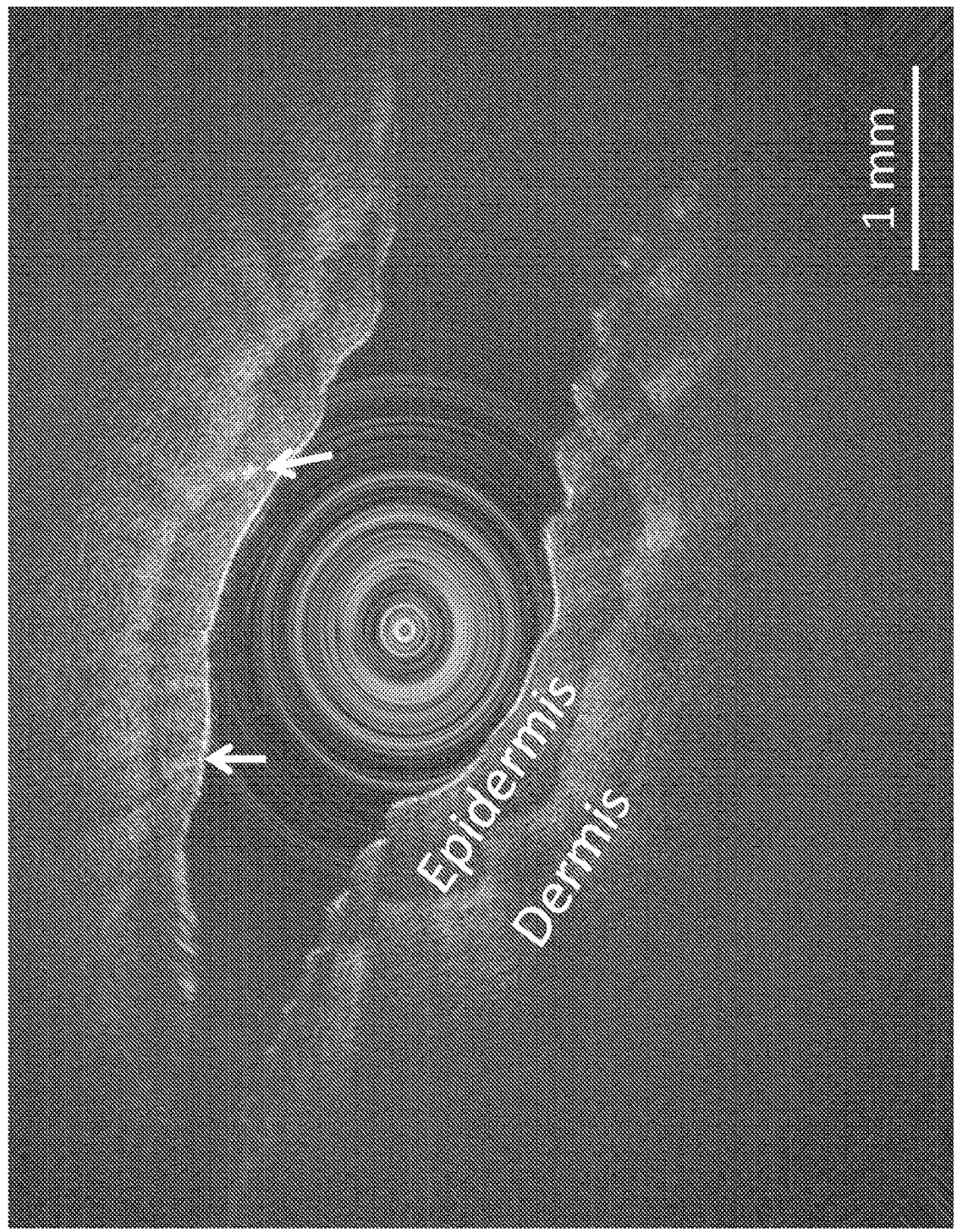
FIG. 11 is an image of fingers holding a distal tip of a common-path optical waveguide probe, as described in Example 1.

An OCT system 110, 210 and common-path optical waveguide probe 305 designed according to the above-referenced design principles was used to acquire an image of fingertips holding the probe 305. The OCT source 201 was a swept source laser. The scan rate was 100 kHz, the central wavelength was 1310 nm, the scan range was 140 nm, and the output power was 34 mW. The reference reflector was tuned to reflect 30 µW of reference signal power. The resulting image is shown in FIG. 11. The layers of skin are clearly identifiable and are identified in the image as epidermis and dermis. Sweat glands were also identifiable and are identified in the image using the arrows.

Example 2

Figure 12:
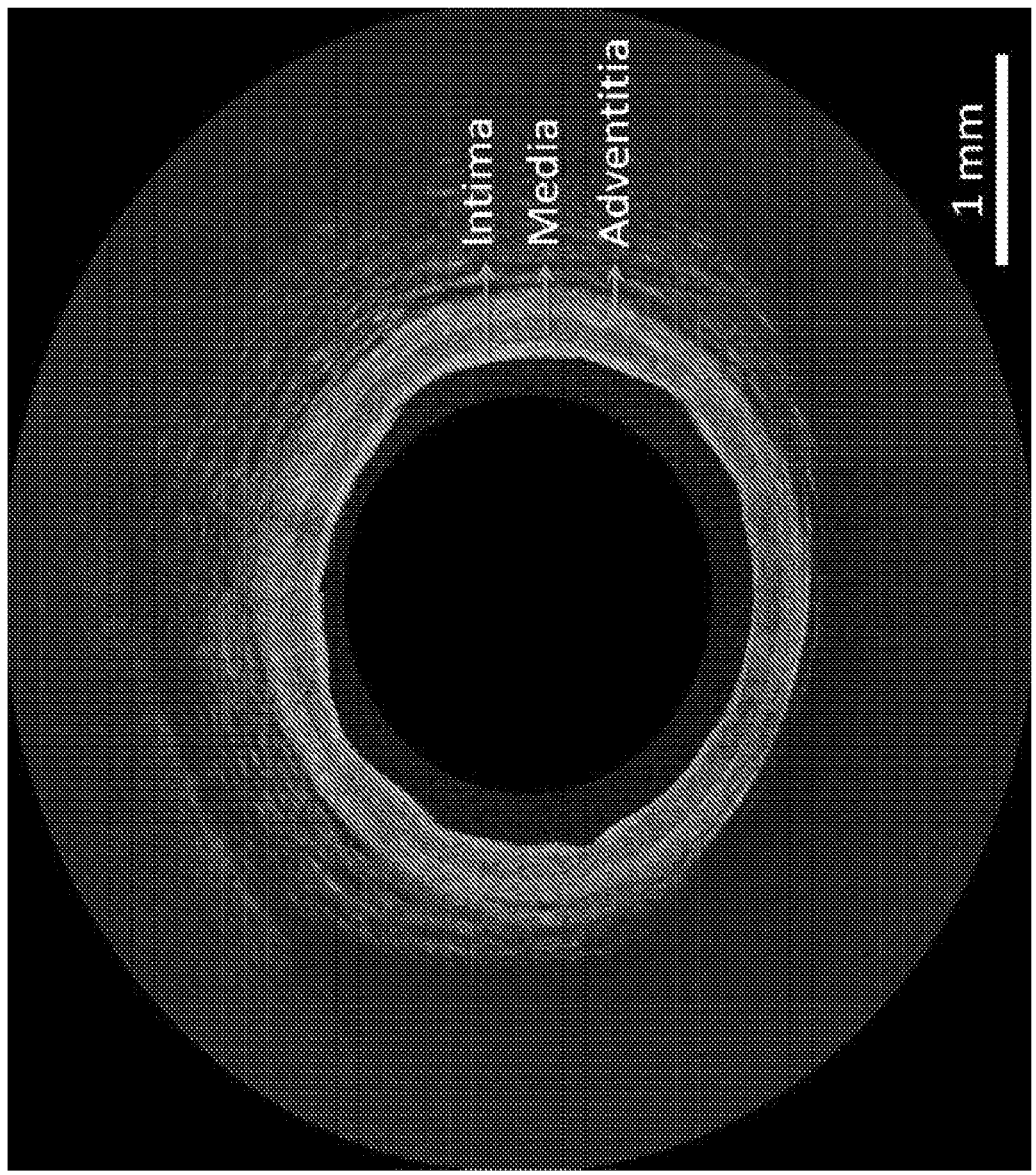
FIG. 12 is an image of a cadaver coronary artery acquired by the systems described herein, as described in Example 2.

An OCT system 110, 210, a common-path optical waveguide probe 305, and a distal tip 419 designed according to the above-referenced design principles was used to acquire an image of a cadaver coronary artery. The OCT source 201 and parameters were the same as Example 1. The probes used are those shown in FIGS. 6 and 7. The resulting image of the cadaver coronary artery is shown in FIG. 12. The layers of the artery are clearly identifiable and are identified in the images as the intima, media, and adventitia.

Example 3

One OCT system 210 without a Michaelson interferometer, such as the one shown in FIG. 2B, and one OCT system 210 having a Michaelson interferometer, such as the one shown in FIG. 2C, a common-path optical waveguide probe, and a distal tip 419 designed according to the above-referenced design principles was used to acquire an image of a finger placed at a distance of 20 cm from the reference reflector. The OCT source 201 and parameters were the same as Example 1. When using the system 210 shown in FIG. 2B, no image was seen because the optical path distance between the sample and the reference reflected was much greater than the imaging depth of the system. However, using the system 210 of FIG. 2C and setting an optical path length difference between the first mirror and the second mirror to approximately 19 cm, an image of the finger appeared in the imaging window.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Indeed, the arrangements, systems, and methods according to the exemplary embodiments of the present disclosure can be used with and/or implemented any OCT system, OFDI system, SD-OCT system or other imaging systems capable of imaging in vivo or fresh tissues, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, U.S. Patent Publication No. 2002/0122246, published on May 9, 2002, U.S. Patent Application 61/649,546, U.S. patent application Ser. No. 11/625,135, and U.S. Patent Application 61/589,083, the disclosures of which are incorporated by reference herein in their entireties. The entire disclosure of each patent and publication cited herein is incorporated by reference, as if each such patent or publication were individually incorporated by reference herein.

We claim:

1. A common-path optical waveguide probe comprising:
   an optical waveguide having a proximal end and a distal end;
   a lens coupled to the distal end;
   a reference reflector positioned between the optical waveguide and the lens; and
   a reflective surface associated with the lens,
   wherein the reference reflector is not glass,
   wherein the waveguide probe is configured to focus light by passage of the light through the reference reflector toward the lens and the reflective surface,
   wherein the light is reflected from the reflective surface toward a sample, and
   wherein the reference reflector comprises a film, wherein the film has an index of refraction that is different from the index of refraction of the optical waveguide, and wherein the index of refraction of the film is configured to cause a predictable selective reflectance.

2. The common-path optical waveguide probe of claim 1, wherein reflectivity of the reference reflector is not based on a difference between indices of refraction of the reference reflector and air.

3. The common-path optical waveguide probe of claim 1, the common-path optical waveguide probe further comprising a spacer positioned between the optical waveguide and the lens, the spacer configured for beam propagation.

4. The common-path optical waveguide probe of claim 1, wherein the film comprises a metal film.

5. The common-path optical waveguide probe of claim 4, wherein the metal film has a thickness of between 1 pm and 1 mm.

6. The common-path optical waveguide probe of claim 4, wherein the metal film comprises a metal selected from the group consisting of gold, silver, aluminum, platinum, or a combination thereof.

7. The common-path optical waveguide probe of claim 1, wherein the film comprises a dielectric film.

8. The common-path optical waveguide probe of claim 7, wherein the dielectric film has a thickness of between 1 pm and 1 mm.

9. The common-path optical waveguide probe of claim 1, wherein the film comprises a non-metal, non-dielectric material film.

10. The common-path optical waveguide probe of claim 9, wherein the non-metal, non-dielectric material film has a thickness of between 1 pm and 1 mm.

11. The common-path optical waveguide probe of claim 1, wherein the optical waveguide is an optical fiber.

12. The common-path optical waveguide probe of claim 11, wherein the optical fiber is a single-mode optical fiber.

13. The common-path optical waveguide probe of claim 11, wherein the optical fiber is a double clad optical fiber.

14. The common-path optical waveguide probe of claim 1, wherein the lens is a ball lens.

15. The common-path optical waveguide probe of claim 1, wherein the lens is a graded index fiber lens.

16. The common-path optical waveguide probe of claim 1, the common-path optical waveguide probe further comprising a driveshaft, wherein the optical waveguide, the lens, the reference reflector, or a combination thereof is coupled to the driveshaft.

17. A catheter comprising:
   the common-path optical waveguide probe of claim 1; and
   a sheath configured to receive the common-path optical waveguide probe.

18. An optical coherence tomography (OCT) system comprising:
   an OCT light source;
   an OCT detector;
   a common-path optical waveguide probe comprising:
      an optical waveguide having a proximal end and a distal end,
      a lens coupled to the distal end, a reference reflector positioned between the optical waveguide and the lens, and a reflective surface associated with the lens, wherein the reference reflector is not glass, wherein the waveguide probe is configured to focus light by passage of the light through the reference reflector toward the lens and the reflective surface, wherein the light is reflected from the reflective surface toward a sample, and wherein the reference reflector comprises a film, wherein the film has an index of refraction that is different from the index of refraction of the optical waveguide, and wherein the index of refraction of the film is configured to cause a predictable selective reflectance;

a circulator coupled to the OCT light source, the OCT detector, and the common-path optical waveguide probe, the circulator configured to direct light from the OCT light source to the common-path optical waveguide probe and from the common-path optical waveguide probe to the OCT detector; and an OCT controller coupled to the OCT detector and configured to provide an OCT signal output representative of an OCT signal measured at the OCT detector.

19. The OCT system of claim 18, wherein the OCT light source is a broadband light source.

20. The OCT system of claim 18, wherein the OCT detector is an OCT spectrometer comprising a collimator, a grating, a spectrometer lens, and a linear array camera.

21. The OCT system of claim 18, the system further comprising a first beamsplitter positioned upstream of the common-path optical waveguide probe, the OCT detector comprising a balanced photodetector, the beamsplitter configured to direct a portion of the light from the OCT light source to the balanced photodetector.

22. A method of making a common-path optical waveguide probe, the method comprising:

splicing together a first end of a first optical waveguide and a second end of a second optical waveguide using laser splicing, wherein at least one of the first end and the second end has a reference reflector precursor positioned at a surface undergoing the splicing, thereby providing a reference reflector between the first optical waveguide and the second optical waveguide, wherein the reference reflector comprises a film, wherein the film has an index of refraction that is different from the index of refraction of the optical waveguide, and wherein the index of refraction of the film is configured to cause a predictable selective reflectance;

forming or attaching a lens to an opposite end of the first optical waveguide that is opposite the first end; and providing a reflective surface associated with the lens.

23. The method of claim 22, wherein forming the lens comprises heating the end opposite the first end and forming a ball lens.

24. The method of claim 22, wherein the intensity and/or duration of the laser splicing is selected to provide a predetermined thickness or reflectivity of the reference reflector.

* * * * *